US010265081B2

(12) United States Patent
Kennedy et al.

(10) Patent No.: US 10,265,081 B2
(45) Date of Patent: Apr. 23, 2019

(54) INTRA-OPERATIVELY ADJUSTABLE CUTTING GUIDE (71) Applicant: Smith & Nephew, Inc., Memphis, TN (US)

(72) Inventors: Eric S. Kennedy, Memphis, TN (US); Zachary C. Wilkinson, Germantown, TN (US); Maroun H. Tarsha, Memphis, TN (US); Randy C. Winebarger, Southaven, MS (US)

(73) Assignee: SMITH & NEPHEW, INC., Memphis, TN (US)

( * ) Notice: Subject to any disclaimer, the term of this patent is extended or adjusted under 35 U.S.C. 154(b) by 530 days.

(21) Appl. No.: 14/420,445

(22) PCT Filed: Aug. 9, 2013

(86) PCT No.: PCT/US2013/054281
§ 371 (c)(1),
(2) Date: Feb. 9, 2015

(87) PCT Pub. No.: WO2014/026085
PCT Pub. Date: Feb. 13, 2014

(65) Prior Publication Data
US 2015/0190144 A1 Jul. 9, 2015

Related U.S. Application Data (60) Provisional application No. 61/681,493, filed on Aug. 9, 2012.

(51) Int. Cl.
A61B 17/58 (2006.01)
A61B 17/60 (2006.01)
(Continued)

(52) U.S. Cl.
CPC .................. A61B 17/157 (2013.01)

(58) Field of Classification Search
CPC combination set(s) only.
See application file for complete search history.

(56) References Cited

U.S. PATENT DOCUMENTS

| 5,234,433 A | 8/1993 | Bert et al. |
| 2001/0001120 A1 | 5/2001 | Masini |

(Continued)

FOREIGN PATENT DOCUMENTS

WO 2012051542 A2 4/2012

OTHER PUBLICATIONS

Australian Patent Office, Examination Report No. 1, dated Mar. 1, 2017, 3 pages.

(Continued)

Primary Examiner — Sameh Boles
(74) Attorney, Agent, or Firm — Pepper Hamilton LLP (57) ABSTRACT A tibial cutting guide includes upper and lower portions having patient-matched surfaces. The upper portion defines resection slots for forming resections about the tibial eminence. The lower portion defines two pin slots for receiving alignment pins such that in use the position of the resection slots relative to the tibial eminence can be adjusted by sliding the cutting guide along the alignment pins placed in the tibia through the pin slots. The lower portion defines a resection slot for guiding a saw blade to form a horizontal plateau resection, and two pin holes for receiving fixation pins. A method includes positioning a patient-matched cutting guide on the proximal tibia; intra-operatively adjusting the position of the cutting guide in two degrees of freedom by sliding the cutting guide along fixation pins placed in the tibia; and resecting the tibia about the tibial eminence.

13 Claims, 10 Drawing Sheets (51) Int. Cl.
*A61F 2/00* (2006.01)
*A61B 17/15* (2006.01)

(56) References Cited

U.S. PATENT DOCUMENTS

| | | | | |
|---|---|---|---|---|
| 2005/0240196 | A1* | 10/2005 | Davis | A61B 17/155 606/87 |
| 2009/0088763 | A1 | 4/2009 | Aram et al. | |
| 2010/0305488 | A1 | 12/2010 | Kecman et al. | |
| 2011/0245835 | A1* | 10/2011 | Dodds | A61B 17/155 606/87 |
| 2014/0066720 | A1* | 3/2014 | Wilkinson | A61B 17/157 600/235 |

OTHER PUBLICATIONS

European Patent Office, European Search Report dated Apr. 29, 2016, 8 pages.
European Patent Office, First Office Action, dated Oct. 24, 2017, 4 pages.
Australian Second Examination Report; Australian Intellectual Property Office; Australian Application No. 2013299495; dated Feb. 6, 2018; 3 pages.
International Search Report; International Searching Authority; International Patent Application No. PCT/US2013/054281; dated Nov. 14, 2013; 6 pages.
International Written Opinion; International Searching Authority; International Patent Application No. PCT/US2013/054281; dated Nov. 14, 2013; 5 pages.
Japanese Patent Office, First Office Action, dated Oct. 24, 2017, 4 pages.
Japanese Decision of Rejection; Japanese Patent Office; Japanese Patent Application No. 2015-526727; dated Feb. 26, 2018; 8 pages.

* cited by examiner

INTRA-OPERATIVELY ADJUSTABLE CUTTING GUIDE

CROSS-REFERENCE TO RELATED APPLICATIONS

This application is a United States National Phase filing of International Application No. PCT/US2013/054281, filed Aug. 9, 2013 which claims priority to and the full benefit of U.S. Provisional Application Ser. No. 61/681,493, filed Aug. 9, 2012, and titled "INTRA-OPERATIVELY ADJUSTABLE CUTTING GUIDE", the entire contents of which are incorporated herein by reference.

BACKGROUND

Cutting guides are used during orthopaedic procedures to insert pins in bone and guide resections to the bone to prepare the bone for receipt of an implant. For example, during bi-cruciate retaining total knee arthroplasty, a cutting guide used to prepare the proximal end of a patient's tibia is designed the leave intact portion of the tibial eminence that function as attachment sites for the anterior and posterior cruciate ligaments.

SUMMARY

A cutting guide for preparing the proximal end of a patient's tibia is described in International Application WO 2012/051542, titled Patient-Matched Instrumentation and Methods, hereby incorporated by reference in its entirety.

A cutting guide can include pin slots that permit the position of the cutting guide to be intra-operatively adjusted relative to pins inserted in the bone through the slots. A bone facing surface of a cutting guide, for example, a cutting guide configured to mount to the proximal end of a patient's tibia, is patient-matched, with the entire surface conforming to the shape of the tibia or select points or regions of the surface conforming to the shape of the tibia. The patient-matched surface of the cutting guide initially restrains the position of the cutting guide when placed on the tibia in five degrees of freedom. After pins are placed in the tibia through the slots, subsequent movement of the cutting guide is restrained in all but two of the degrees of freedom. Movement in the two degrees of freedom permits fine tuning of the position of the cutting guide to align eminence resection slots of the cutting guide relative to the tibial eminence.

According to one aspect, a tibial cutting guide includes an upper portion having a patient-matched surface and a lower portion having a patient-matched surface. The upper portion defines resection slots for forming resections about the tibial eminence. The lower portion defines two pin slots for receiving alignment pins such that in use the position of the resection slots relative to the tibial eminence can be adjusted by sliding the cutting guide along the alignment pins placed in the tibia through the pin slots.

Embodiments of this aspect may include one or more of the following features. The lower portion defines a resection slot for guiding a saw blade to form a horizontal plateau resection. The lower portion defines two pin holes for receiving fixation pins.

According to another aspect, a method includes positioning a patient-matched cutting guide on the proximal tibia; intra-operatively adjusting the position of the cutting guide in one rotation and at least one translation degree of freedom by sliding the cutting guide along fixation pins placed in the tibia through pin slots defined in the cutting guide; and resecting the tibia about a tibial eminence using a blade guided by resection slots of the cutting guide.

The details of one or more embodiments are set forth in the accompanying drawings and the description below. Other features, objects, and advantages will be apparent from the description and drawings, and from the claims.

DETAILED DESCRIPTION

Referring to FIGS. 1-5, a cutting guide 10 for preparing a proximal tibia for receipt of an implant during bi-cruciate retaining total knee arthroplasty includes an upper portion 12 with paddles 40, 42 having patient-matched conforming surfaces 14 for contacting the proximal surface of the tibia, and a lower portion 16 having a patient-matched conforming surface 18 for contacting the medial side of the anterior face of the proximal end of the tibia.

Figure 15:
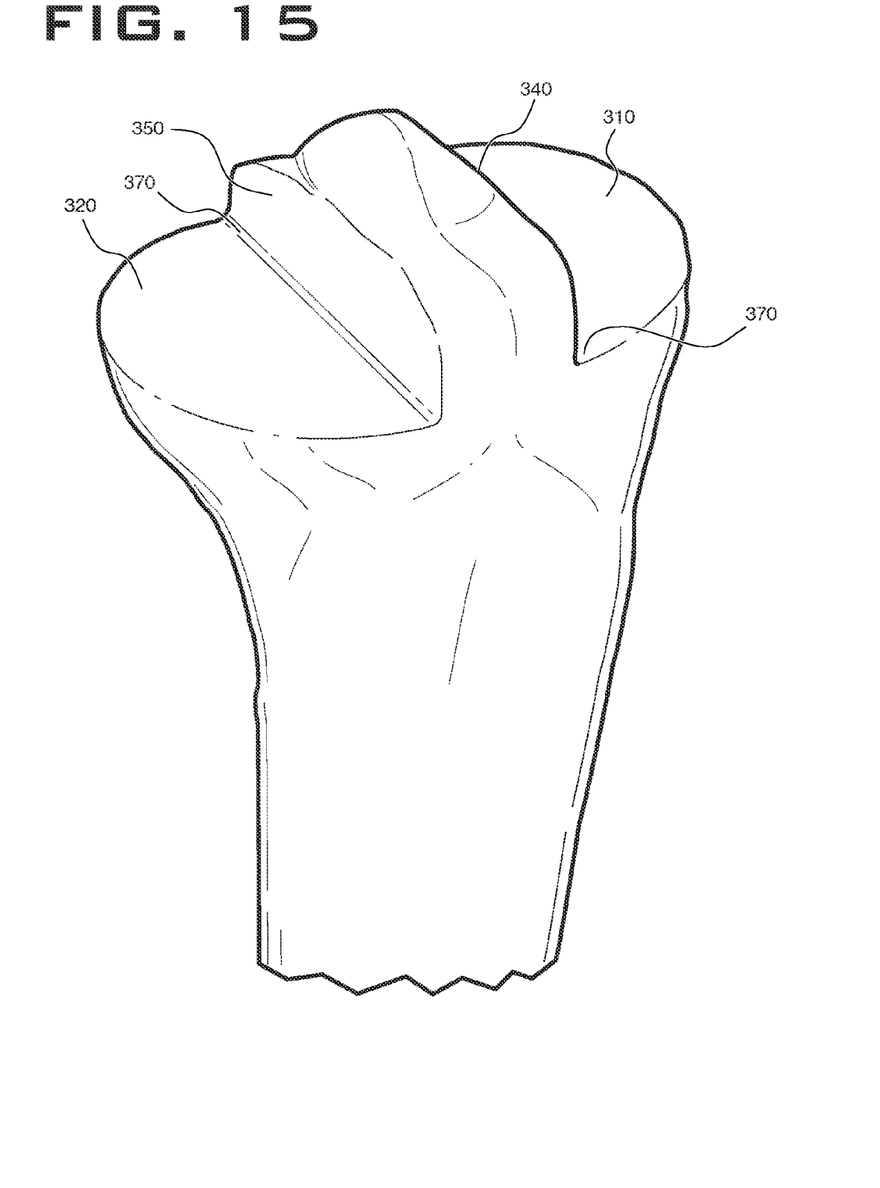
FIG. 15 illustrates a tibia after plateau and eminence resections have been made.

The lower portion 16 defines a resection slot 20 for guiding a saw blade to form horizontal medial and/or lateral plateau resections 310, 320 (FIG. 15). The upper portion 12 defines resection slots 22, 24 for guiding a saw blade to form medial and lateral vertical eminence resections 340, 350 (FIG. 15). The lower portion 16 defines two pin slots 26, 28 through which alignment pins 30, 32 are placed in the tibia, and two pin holes 34, 36 through which fixation pins (not shown) are placed in the tibia.

In use, the cutting guide 10 is placed on the patient's tibia with the patient-matched surfaces 14, 18 of the cutting guide 10 initially restraining the position of the cutting guide in six degrees of freedom. The pins 30, 32 are placed in the tibia through the slots 26, 28. The operator can slide the cutting guide 10 relative to the pins 30, 32 in the slots 26, 28 in three degrees of freedom, i.e., internal-external rotation (disproportionate movement along the axis of the pins), medial-lateral translation (side-to-side movement such that the pins can be at any location from one end to the opposite end of the slots), and anterior-posterior translation (proportionate movement along the axis of the pins) to intra-operatively adjust the alignment of the eminence resection slots 22, 24 relative to the tibial eminence. Movement in internal-external rotation and at least medial-lateral translation permits fine tuning of the position of the cutting guide to align the eminence resection slots.

Because typical patient-matched instrumentation seeks to fix all degrees of freedom simultaneously, any error or deviation in any degree of freedom has a negative impact on the other degrees of freedom. One common example is when an operator determines that a particular rotation or a particular slope is desirable, but that particular selection is not what may be suggested by the constraint of the instrument. In altering rotation, slope may be affected in that less or greater slope is induced. Likewise, lesser or greater varus angle may be induced and/or medial or lateral depth may increase or decrease. But, if an operator has the capability to alter some or all degrees of freedom after the initial placement of the patient-matched instrument, the operator is much less likely to attempt to affect a change to the alignment suggested by the conformity/constraint of the patient-matched instrument.

In some instances it may be advantageous for an operator to pre-operatively request longer slot lengths thus affording the operator more freedom to place pins through the slots in intra-operatively determinable locations/orientations or more freedom to intra-operatively adjust the patient-matched instrument on the pins. In other instances, it may be advantageous for an operator to pre-operatively request shorter, more constraining slot lengths for operators who desire the patient-matched instrument to limit potentially inappropriate movement of the patient-matched instrument or who desire the pins to be maximally spaced apart so as to provide maximum varus/valgus constraint.

Figure 6:
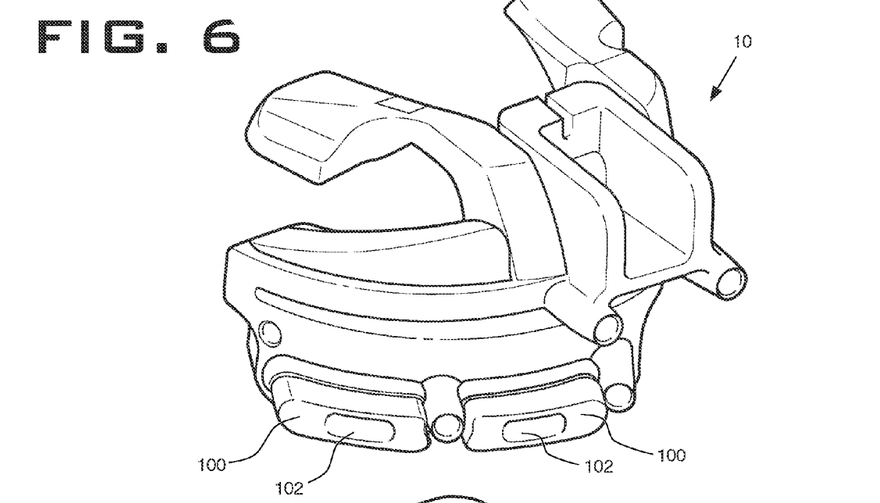
FIGS. 6 and 7 illustrate pin guide limiters for the cutting guide.
Figure 7:
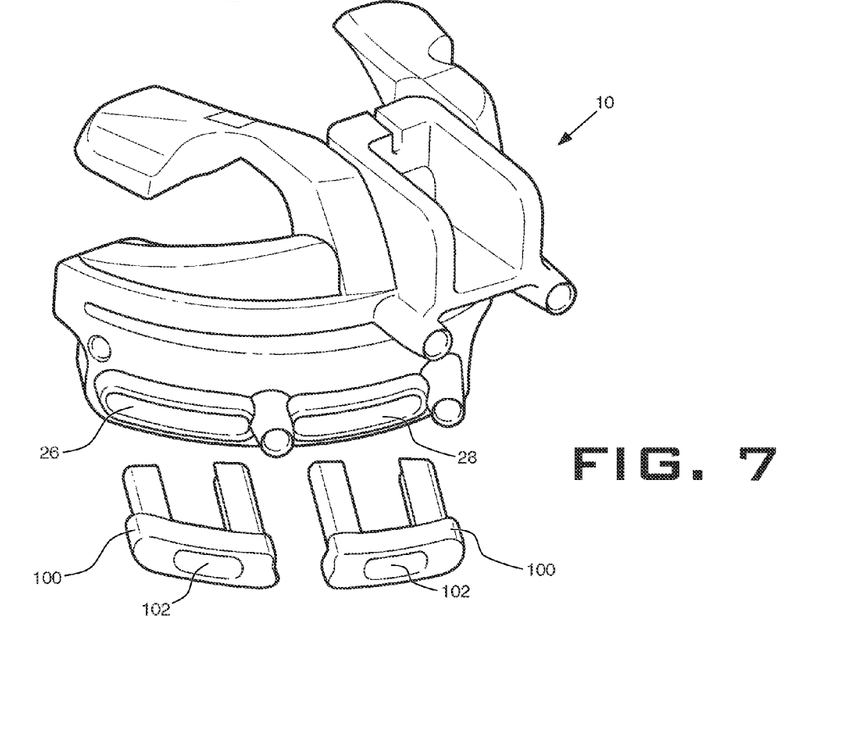
Figure 8:
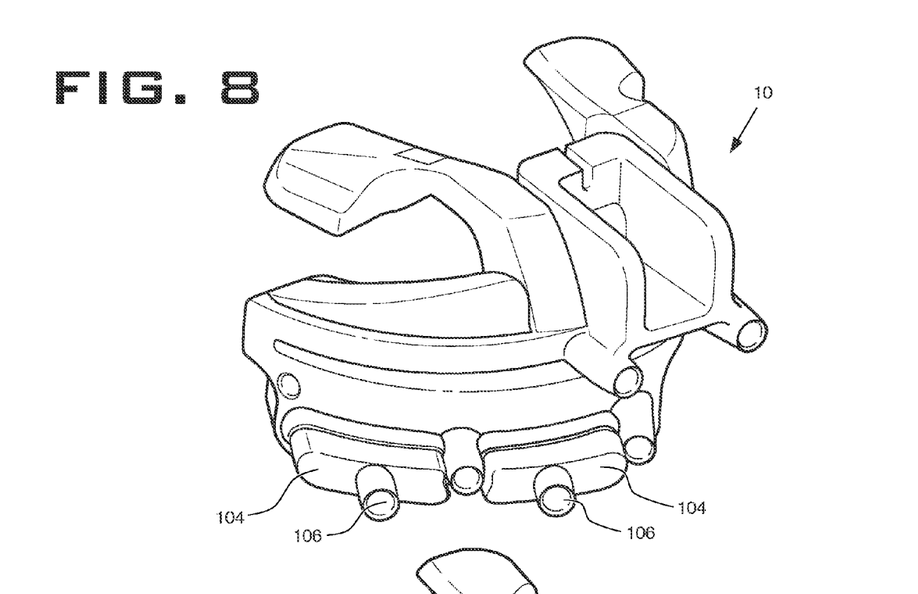
FIGS. 8 and 9 illustrate additional pin guide limiters for the cutting guide.
Figure 9:
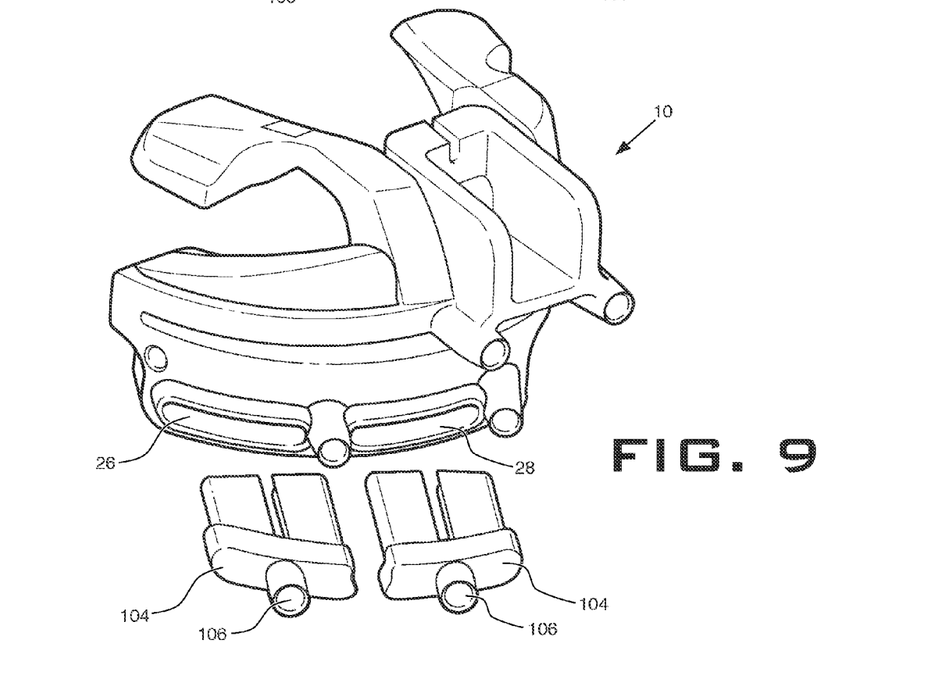

Referring to FIGS. 6 and 7, in other instances where it is unknown what slot length may be needed, removable pin guide limiters 100 can be included with the patient-matched instrument. The pin guide limiters fit inside slots 26, 28 and each define a slot 102 that is shorter than slots 26, 28. The pin guide limiters 100 serve to constrain the amount of fine-tune adjustment but can be removed should the operator decide more freedom is needed. Referring to FIGS. 8 and 9, in the special case where the operator desires no freedom for fine-tune adjustment, rather than being slotted, removable pin guide limiters 104 each define a pin hole 106 to provide maximum constraint. The removable pin guide limiters 104 have an alternate use for operators who desire exact positioning of the pins inside the slots 26, 28. By first using the removable pin guide limiters 104, the operator can be certain that subsequent movement of each slot 26, 28 relative to each pin is limited as was intended by the pre-operative plan.

The decision regarding the length of the slot in regards to the freedom or constraint of intraoperative adjustment of the patient-matched instrument depends upon the operator's preference for anatomical reference priority. In cases where the operator is more concerned with matching the alignment of the eminence with that of the femur in flexion and/or extension rather than achieving best fit and coverage, the operator will likely elect the longer slot length. Should the operator value best fit and coverage over alignment with the femur, likely the choice would be for a more constraining pin slot. If uncertain, likely the choice will be for a removable pin guide limiter.

In some cases there is a desire to fine tune adjust other degrees of freedom whether pre or post resection. After internal-external rotation and medial-lateral translation, the most commonly adjusted tibial degree of freedom is slope (flexion-extension angle of the resection). In the case of bi-cruciate retaining patient-matched devices, the more common instance of tibial slope adjustment is post-resection for purposes of balancing soft tissue constraint in flexion and extension, but there are instances where a slope adjustment can be foreseen prior to the tibial resection due to existing patient conditions or particular surgical decisions made with respect to the femur resections. Adjustment of tibial posterior slope whether before or after the resection is made is a common practice across all tibial replacement procedures. Typically with patient-matched instruments, alternative decisions to those encoded within the patient-matched instrument must be accomplished through a standard reusable non-patient-matched device. Having such devices on hand for what-if scenarios reduces the potential value of patient-matched disposable instrumentation which is cost reduction and procedure simplification.

Figure 1:
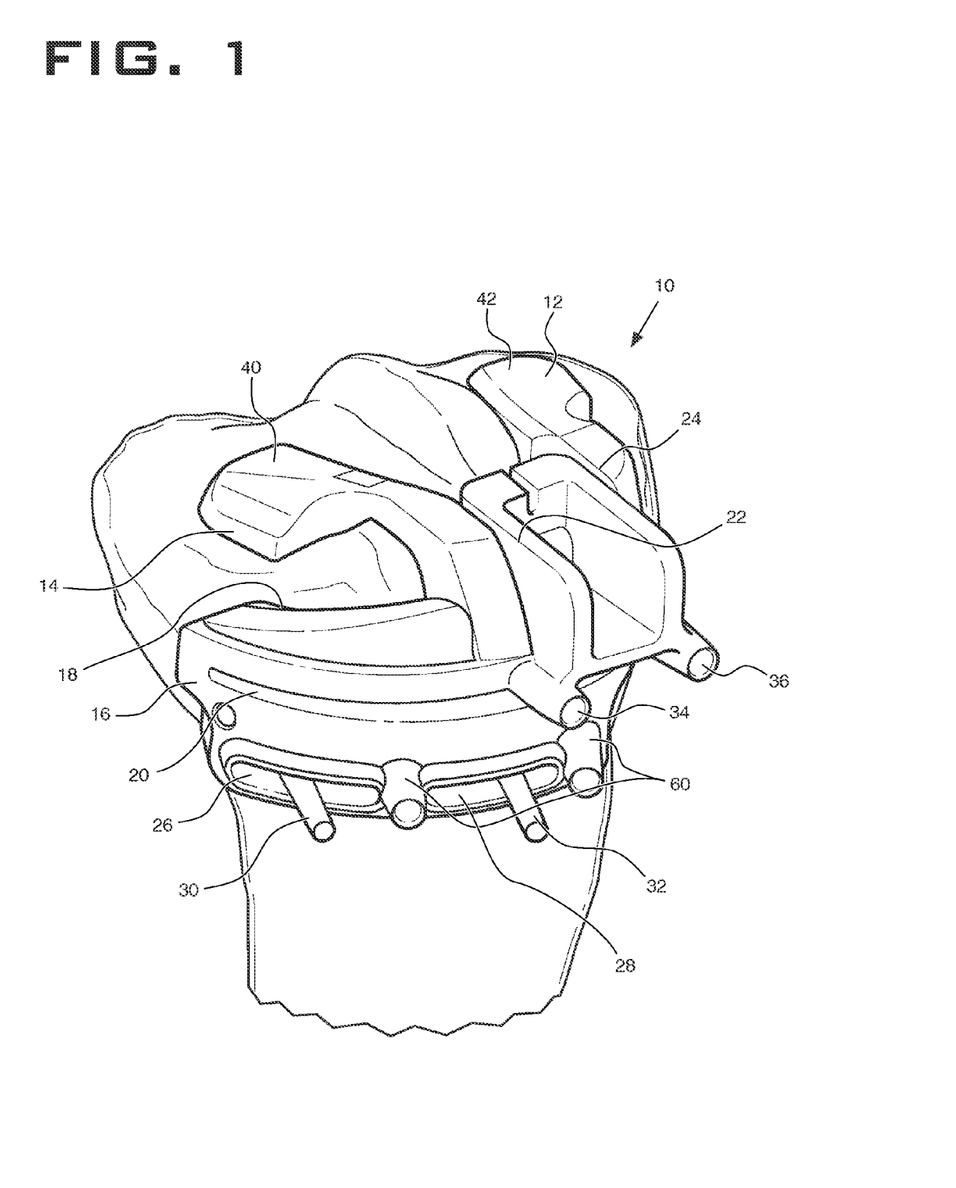
FIG. 1 is an illustration of a cutting guide positioned on a proximal tibia.
Figure 2:
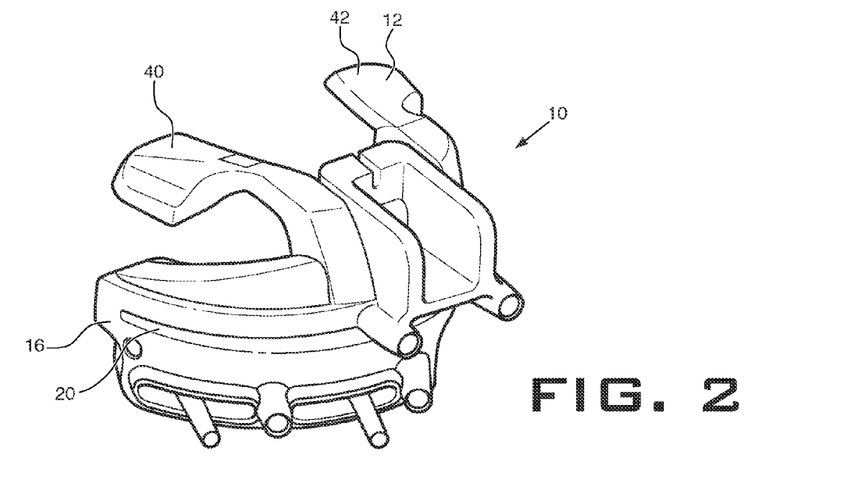
FIGS. 2-5 are various isometric views of the cutting guide.
Figure 3:
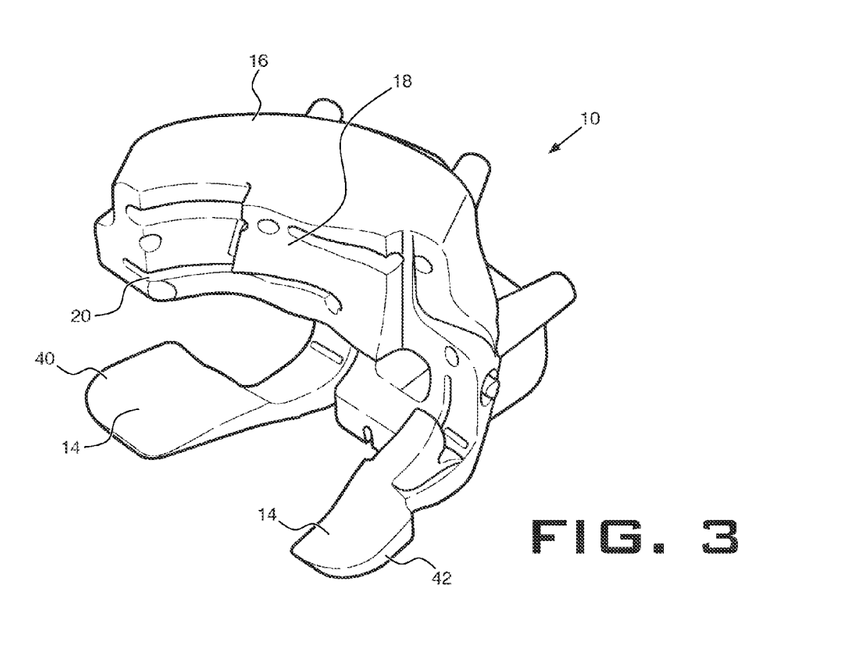
Figure 4:
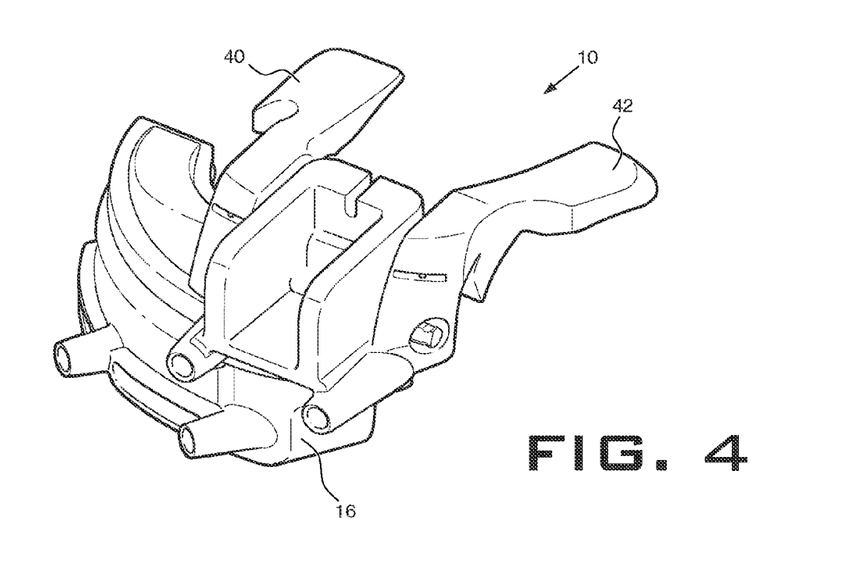
Figure 5:
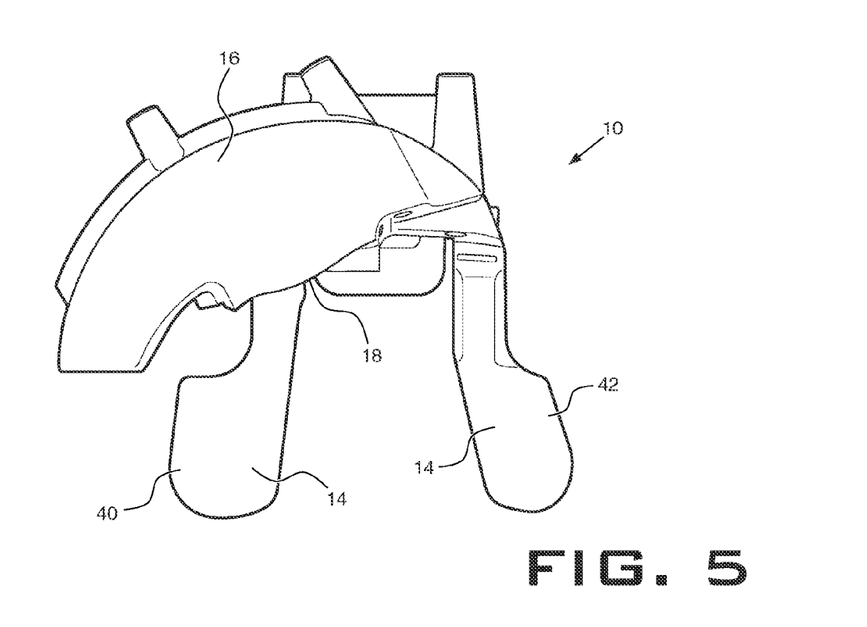

Since procedures are by nature complex due the presence of what-if scenarios, it is therefore advantageous for the patient-matched instrument itself to be able to overcome what-if scenarios such as adjustment of the tibial posterior slope. Referring to FIG. 1, the cutting guide 10 includes a built-in pin guide set 60 constructed at an alternative slope angle which can be used to place an alternative pin set for resetting the posterior slope of the patient-matched instrument. The cutting guide 10 can include additional pin guide sets constructed at additional alternative slope angles. Such pin guide sets are angled and positioned so as to ensure that the new orientation of the saw guide effectively pivots about an axis orthogonal to the mechanical axis and the selected internal-external rotation axis and anterior to the anterior-posterior midline of the tibia.

Figure 10:
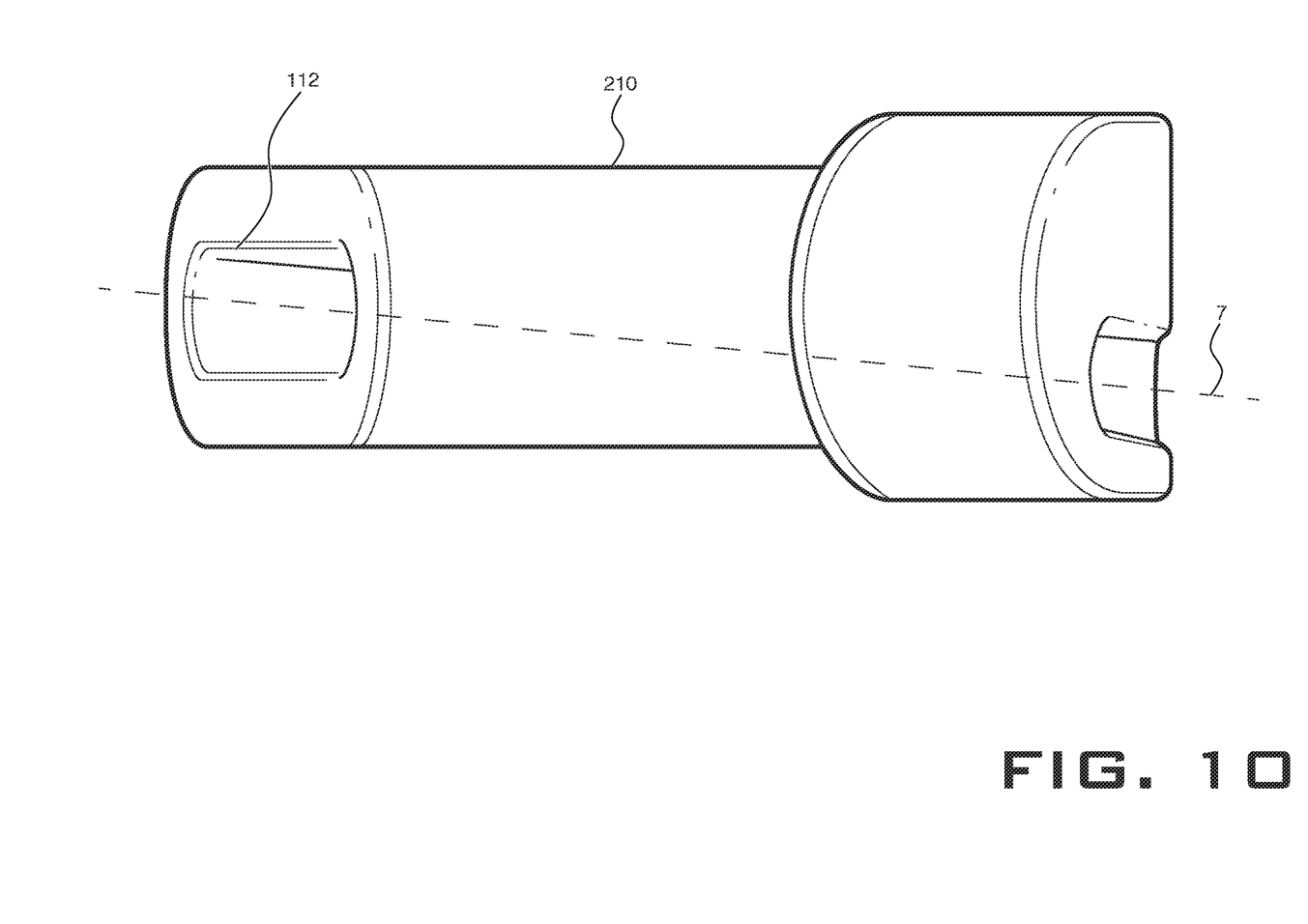
FIG. 10 is a side view of a sloped pin guide.
Figure 11:
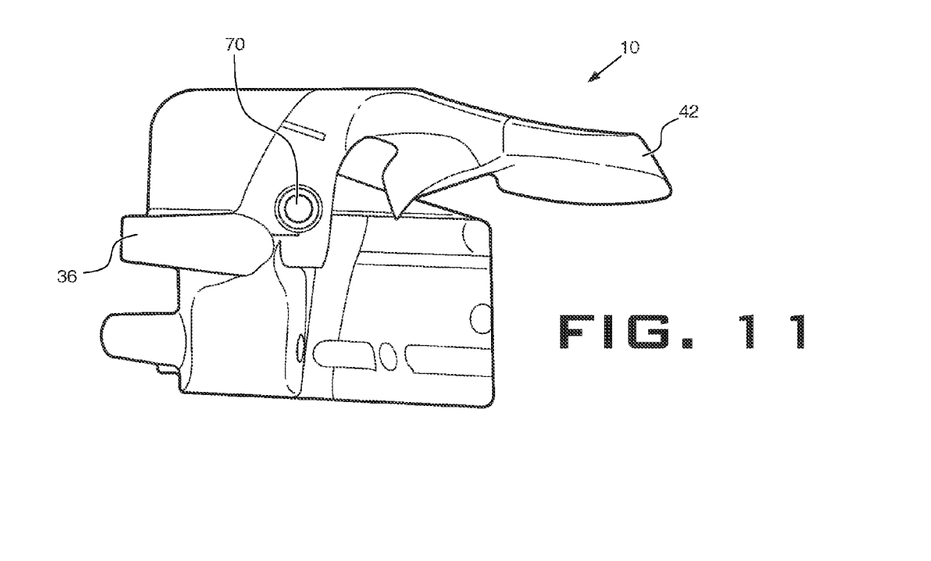
FIGS. 11-14 illustrate a stop pin used with the cutting guide.

Referring to FIG. 10, alternative removable pin guide sets 110 that vary in slope are another way of adjusting posterior tibial slope without the need to place alternative pin sets in the tibia. Each of the pin guide sets has a pin hole 112 oriented at a different posterior-anterior slope X. By designing the built-in slots 26, 28 to be larger to enable receipt of a pin guide 110, an operator can alter the slope of the patient-matched instrument simply by selecting a particular pin guide set 110 and attaching it to the patient-matched instrument. With a new pin guide set 110 in place, the patient-matched instrument will guide the saw blade in the new orientation dictated by the slope of the pin guide set. To preserve the patient-matched function of the assembly, the pin guides 110 can include surfaces which to some degree conform to the patients' anatomy. Removable pin guides can be constructed to enable the adjustment of slope, depth, varus/valgus, rotation, translation or any combination thereof. Once the operator is satisfied with the particular choice of pin guide, subsequent steps can proceed as normal. In one example, an operator selects a pin guide including a slot. When the patient-matched assembly is placed onto the pins and the bone, the patient-matched surfaces of the pin guide provide helpful constraint to aid the operator in the selection of a particular rotation and translation which will achieve best fit and coverage.

Referring to FIGS. 11-14, cutting guide 10 defines a pin hole 70 for receiving a stop pin 72. When inserted in the pin hole 70, the stop pin 72 serves as a reciprocating saw blade stop to prevent cutting of the guide 10 by the saw blade. The stop pin 72 is intra-operatively insertable and removable from the guide 10.

After the operator is satisfied with the alignment of the medial and/or lateral plateau and eminence resection slots 22, 24, the operator places fixation pins into the tibia through the pin holes 34, 36 to fix the position of the cutting guide 10 in all relevant degrees of freedom.

Referring to FIG. 15, the pin holes 34, 36 are positioned relative to the resection slots 22, 24 such that in use pins placed in the tibia through the holes 34, 36 are positioned at the intersection of the horizontal plateau resections 310, 320 and the vertical eminence resections 340, 350, creating curved sections 370 at the intersections.

The upper portion 12 has, for example, webs 80 (FIG. 12), the enable the operator to cut the paddles 40, 42 off the cutting guide 10. By removing the paddles 40, 42, the operator can evaluate the position of the resection slot 20 prior to making the plateau resections by aligning the cutting guide with a femoral trial or native uncut femur in flexion or extension.

Figure 12:
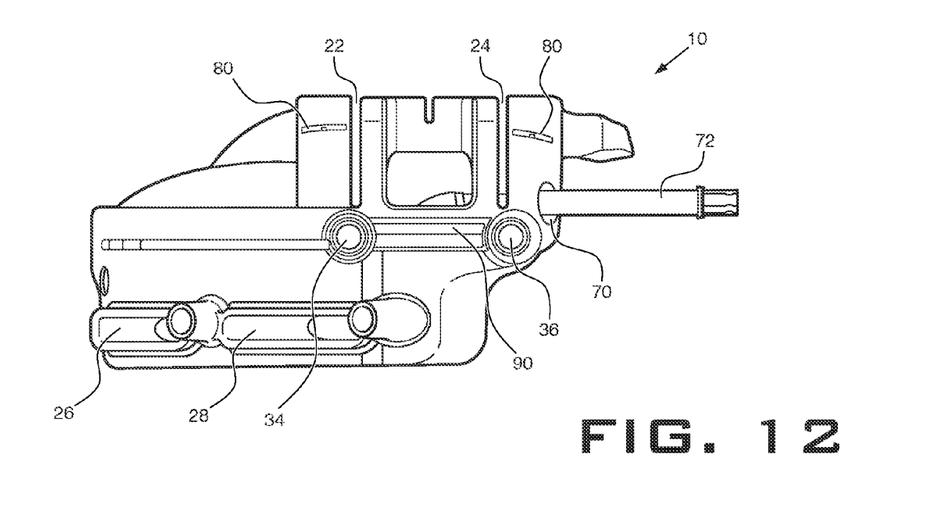
Figure 13:
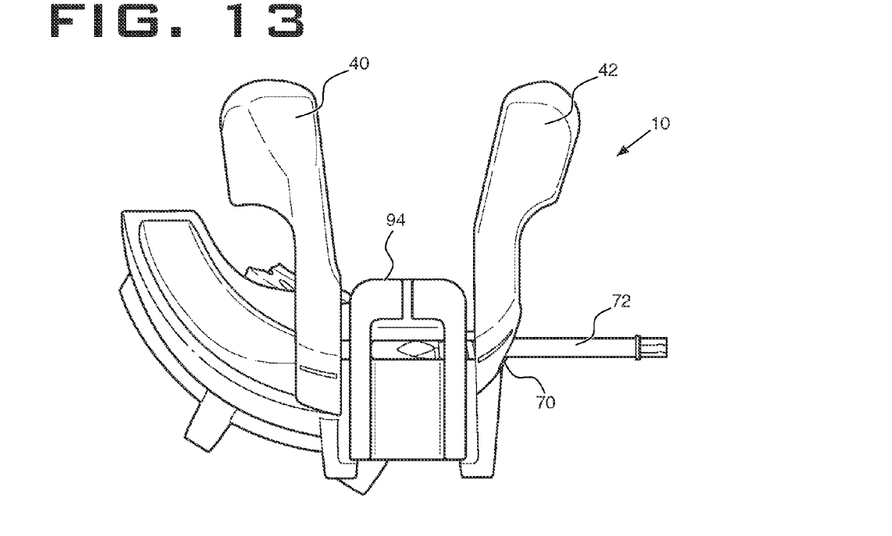
Figure 14:
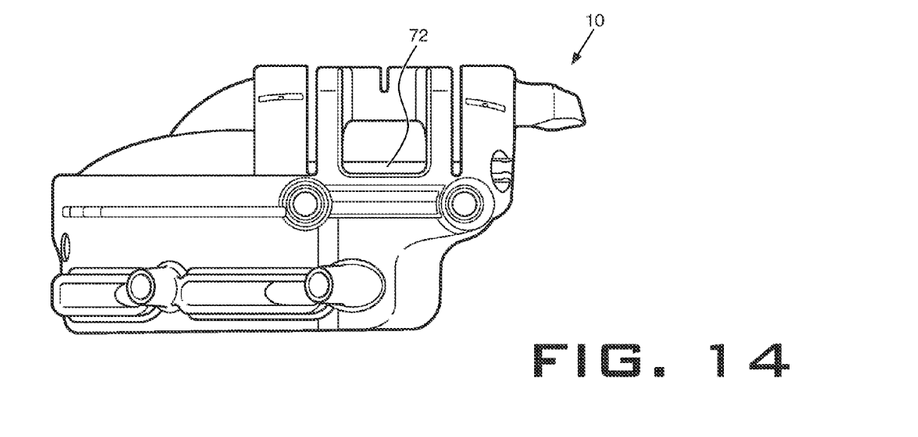
Figure 16:
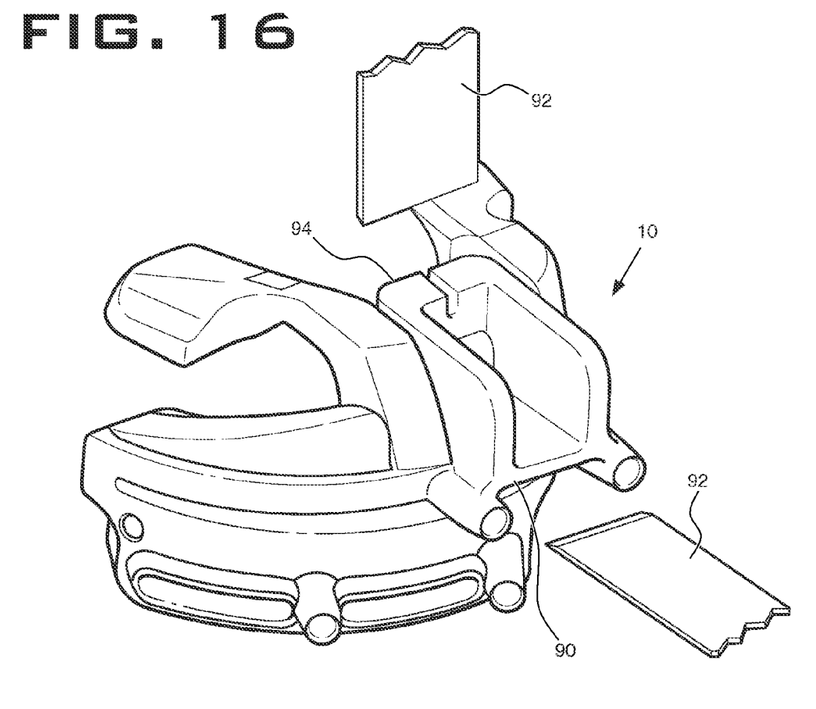
FIG. 16 illustrates making additional eminence resections.

Referring to FIGS. 12 and 16, to make anterior eminence resections, the cutting guide 10 defines an anterior eminence resection slot 90 for receiving a saw blade 92 and a guide surface 94 for guiding the saw blade 92.

Other embodiments are within the scope of the following claims. For example, rather than the patient-matches surfaces 14, 18 being conforming surfaces, one or both of the surfaces can include select points or regions of the surface that conform to the shape of the tibia.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A tibial cutting guide, comprising:
   an upper portion having a patient-matched tibial-plateau surface, the upper portion defining superior-inferior resection slots for forming resections about the tibial eminence;
   a lower portion having a patient-matched tibial anterior-face surface, the lower portion defining at least one of a medial plateau resection slot or a lateral plateau resection slot, and two alignment pin slots for receiving alignment pins, at least one of the two alignment pin slots being located at a distal position relative to the medial plateau resection slot or the lateral plateau resection slot, wherein in use the position of the superior-inferior resection slots relative to the tibial eminence can be adjusted by sliding the cutting guide along alignment pins placed in the tibia through the alignment pin slots; and
   a stop pin hole sized to receive a stop pin which, prevents a saw blade in the medial plateau resection slot or the lateral plateau resection slot from cutting the tibial cutting guide.

2. The tibial cutting guide of claim 1 wherein the lower portion defines two fixation pin holes.

3. The tibial cutting guide of claim 1, wherein each of the two alignment pin slots are at a distal position that extends beneath the medial plateau resection slot or the lateral plateau resection slot.

4. The tibial cutting guide of claim 1, further including at least one pin guide limiter sized for selective placement within at least one alignment pin slot of the two alignment pin slots, the at least one pin guide limiter having a limiter slot sized to receive an alignment pin, the limiter slot having a length in the medial-lateral direction that is shorter than a length of the at least one alignment pin slot in the medial-lateral direction.

5. The tibial cutting guide of claim 4, wherein the limiter slot extends through the at least one pin guide limiter along a first slope, and the at least one alignment pin slot extends through the tibial cutting guide along a second slope, the first slope being different than the second slope.

6. A tibial cutting guide, comprising:
   an upper portion, the upper portion comprising at least two paddles, wherein each paddle has a patient-matched tibial-plateau conforming surface, the upper portion further comprising a medial resection vertical slot and a lateral resection vertical slot;
   a lower portion, the lower portion comprising a patient-matched conforming surface, wherein the patient-matched conforming surface matches a medial side of an anterior face of a proximal end of the tibia, the lower portion further comprising at least one plateau resection slot sized and positioned in the lower portion and extending from a position adjacent the tibial eminence to one of the lateral side or medial side of the tibia, at least two alignment pin slots located at a distal position relative to the at least one plateau resection slot, and at least two fixation pin holes, wherein, in use, a position of the medial and lateral resection slots relative to the tibial eminence can be adjusted by sliding the cutting guide along alignment pins placed in the tibia through the alignment pin slots; and
   at least one pin guide limiter having a limiter slot having a length in the medial-lateral direction that is shorter than a length of the at least one alignment pin slot in the medial-lateral direction.

7. The tibial cutting guide of claim 6, wherein the limiter slot extends through the at least one pin guide limiter along a first slope, and the at least one alignment pin slot extends through the tibial cutting guide along a second slope, the first slope being different than the second slope.

8. The tibial cutting guide of claim 6, further including a stop pin hole sized to receive insertion of a stop pin at a location at which, during use, prevents a saw blade in the at least one plateau resection slot from cutting the tibial cutting guide.

9. The tibial cutting guide of claim 6, wherein at least one fixation pin hole of the at least two fixation pin holes is positioned about the lower portion of the tibial cutting guide at a location at which a pin received in the at least one fixation pin hole forms a curvature in the tibia at an intersection of slots formed in the tibia using (1) the medial resection vertical slot and the at least one plateau resection slot, or (2) the lateral resection vertical slot and the at least one plateau resection slot.

10. A tibial cutting guide, comprising:
    an upper portion with at least two paddles, each paddle having a patient-matched conforming surface that matches a proximal surface of the tibia, the upper portion defining a medial resection vertical slot and a lateral resection vertical slot for forming resections about the tibial eminence;
    a lower portion having a patient-matched conforming surface, wherein the patient-match conforming surface matches a medial side of an anterior face of a proximal end of the tibia, the lower portion defining a plateau resection slot for guiding a saw blade to form at least one of medial and lateral resections that extend through at least one of the medial side or lateral side of the tibia, the lower portion further defining at least two alignment pins slots and at least two fixation pin holes, the at least two alignment slots being distal to and extending at least partially beneath the plateau resection slot, wherein, in use, the position of the resection slots relative to the tibial eminence can be adjusted by sliding the cutting guide along alignment pins placed in the tibia through the alignment pin slots; and wherein at least one fixation pin hole of the at least two fixation pin holes is positioned about the lower portion of the tibial cutting guide such that a pin received in the at least one fixation pin hole forms a curvature in the tibia at an intersection of slots formed in the tibia using (1) the medial resection vertical slot and the plateau resection slot, or (2) the lateral resection vertical slot and the plateau resection slot.

11. The tibial cutting guide of claim 10, further including at least one pin guide limiter that is sized for removable insertion in at least one alignment pin slot of the two alignment pin slots, the at least one pin guide limiter having a limiter slot for receiving an alignment pin, the limiter slot having a medial-lateral length that is shorter than a medial-lateral length of the at least one alignment pin slot.

12. The tibial cutting guide of claim 11, wherein the limiter slot extends through the at least one pin guide limiter along a first slope, and the at least one alignment pin slot extends through the tibial cutting guide along a second slope, the first slope being different than the second slope.

13. The tibial cutting guide of claim 10, further including a stop pin hole sized to receive insertion of a stop pin at a location at which, during use, prevents a saw blade being guided through the plateau resection slot from cutting the tibial cutting guide.

\* \* \* \* \*